United States Patent
Graw

(10) Patent No.: US 9,743,900 B2
(45) Date of Patent: Aug. 29, 2017

(54) MEDICAL IMAGING SYSTEM WITH INTEGRATED BODY MONITORING DEVICE

(75) Inventor: Ansgar Graw, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1847 days.

(21) Appl. No.: 11/158,639

(22) Filed: Jun. 22, 2005

(65) Prior Publication Data

US 2005/0288572 A1    Dec. 29, 2005

Related U.S. Application Data

(60) Provisional application No. 60/583,441, filed on Jun. 28, 2004.

(51) Int. Cl.
| | |
|---|---|
| A61B 5/00 | (2006.01) |
| A61B 6/00 | (2006.01) |
| A61B 5/055 | (2006.01) |
| A61B 8/08 | (2006.01) |
| A61B 8/00 | (2006.01) |

(52) U.S. Cl.
CPC ............ A61B 6/541 (2013.01); A61B 6/4258 (2013.01); *A61B 5/055* (2013.01); *A61B 6/503* (2013.01); *A61B 8/0883* (2013.01); *A61B 8/543* (2013.01)

(58) Field of Classification Search
USPC .......................... 600/407, 411, 427, 428, 436; 250/363.02, 363.03, 363.04
See application file for complete search history.

(56) References Cited

U.S. PATENT DOCUMENTS

| | | | | |
|---|---|---|---|---|
| 4,033,335 A | * | 7/1977 | Nickles ........................ | 600/436 |
| 4,245,646 A | * | 1/1981 | Ionnou et al. ................ | 600/407 |
| 4,991,580 A | * | 2/1991 | Moore ......................... | 600/509 |
| 5,199,438 A | * | 4/1993 | Pearlman ..................... | 600/483 |
| 5,464,014 A | * | 11/1995 | Sugahara ..................... | 600/411 |
| 5,800,355 A | * | 9/1998 | Hasegawa .................... | 600/436 |
| 5,991,947 A | * | 11/1999 | Lavin et al. ..................... | 5/600 |
| 6,148,229 A | * | 11/2000 | Morris, Sr. ............ | A61B 5/055 600/411 |
| 6,205,355 B1 | * | 3/2001 | Lomanto et al. ............ | 600/509 |
| 6,266,553 B1 | * | 7/2001 | Fluhrer et al. ............... | 600/428 |
| 6,501,979 B1 | * | 12/2002 | Manning et al. ............. | 600/413 |
| 6,704,592 B1 | * | 3/2004 | Reynolds et al. ............ | 600/411 |
| 6,713,766 B2 | * | 3/2004 | Garrard et al. .......... | 250/363.02 |
| 7,026,623 B2 | * | 4/2006 | Oaknin et al. ........... | 250/363.04 |
| 7,490,377 B2 | * | 2/2009 | Ahlman ...................... | 5/81.1 R |

(Continued)

*Primary Examiner* — Amanda Lauritzen Moher

(57) ABSTRACT

In some preferred embodiments, a medical imaging system with an integrated body monitoring device is disclosed which includes: a movable platform for supporting a patient during image acquisition; an image acquisition device for the acquisition of images of the patient upon the platform; a body monitoring device for the monitoring of a body function of the patient during image acquisition; the body monitoring device being adapted to transmit body function signals to the image acquisition device and the image acquisition device being adapted to effect image acquisition based on the signals received from the body monitoring device; wherein the body monitoring device is integrated with the image acquisition system. In the preferred embodiments, the medical imaging system is a nuclear medical imaging system and the body monitoring device is an ECG device.

26 Claims, 6 Drawing Sheets

(56) References Cited

U.S. PATENT DOCUMENTS

| | | | |
|---|---|---|---|
| 2003/0216641 A1* | 11/2003 | Acharya et al. | 600/428 |
| 2004/0186358 A1* | 9/2004 | Chernow | A61B 5/0002 600/300 |
| 2007/0016034 A1* | 1/2007 | Donaldson | 600/437 |
| 2007/0055145 A1* | 3/2007 | Zelnik et al. | 600/428 |

* cited by examiner

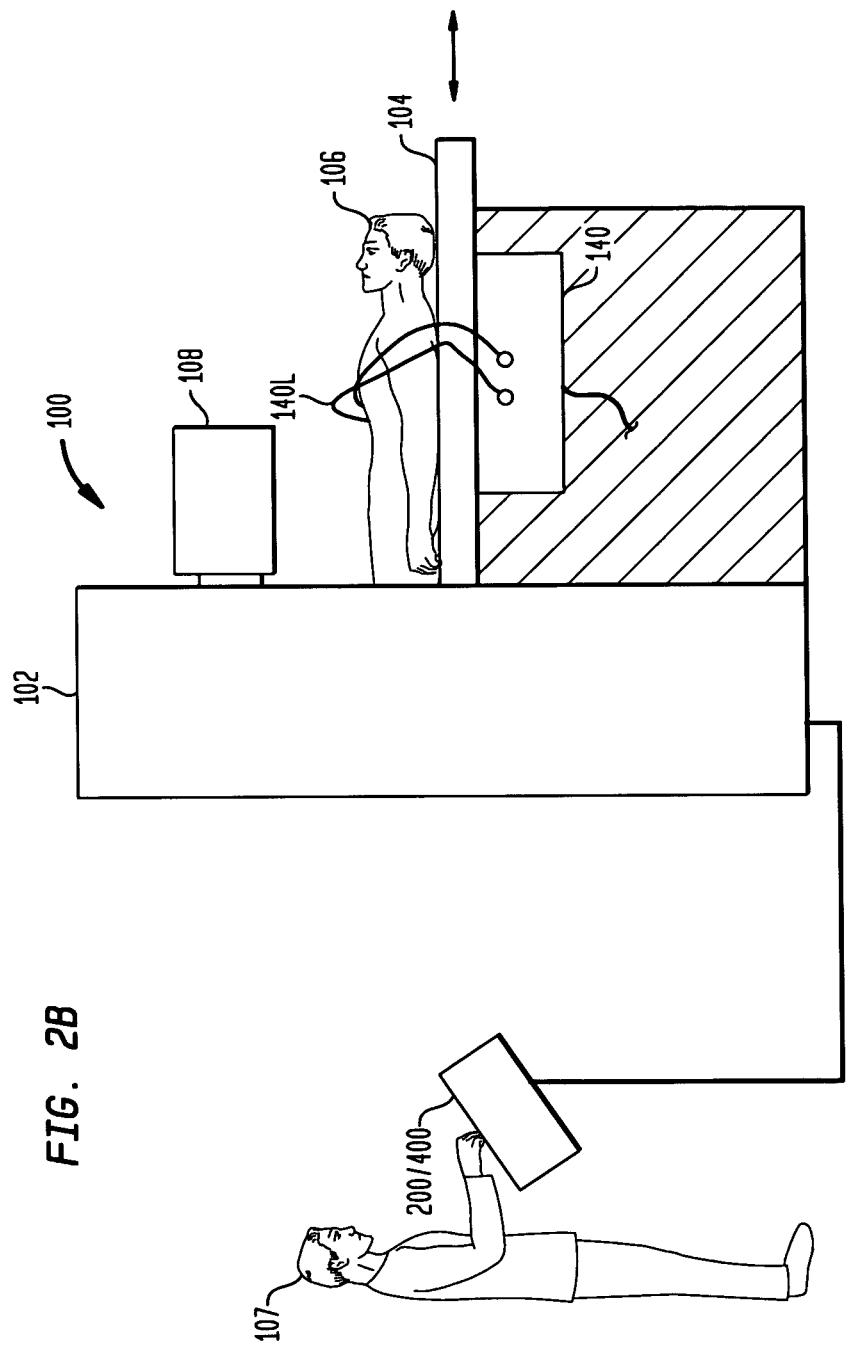

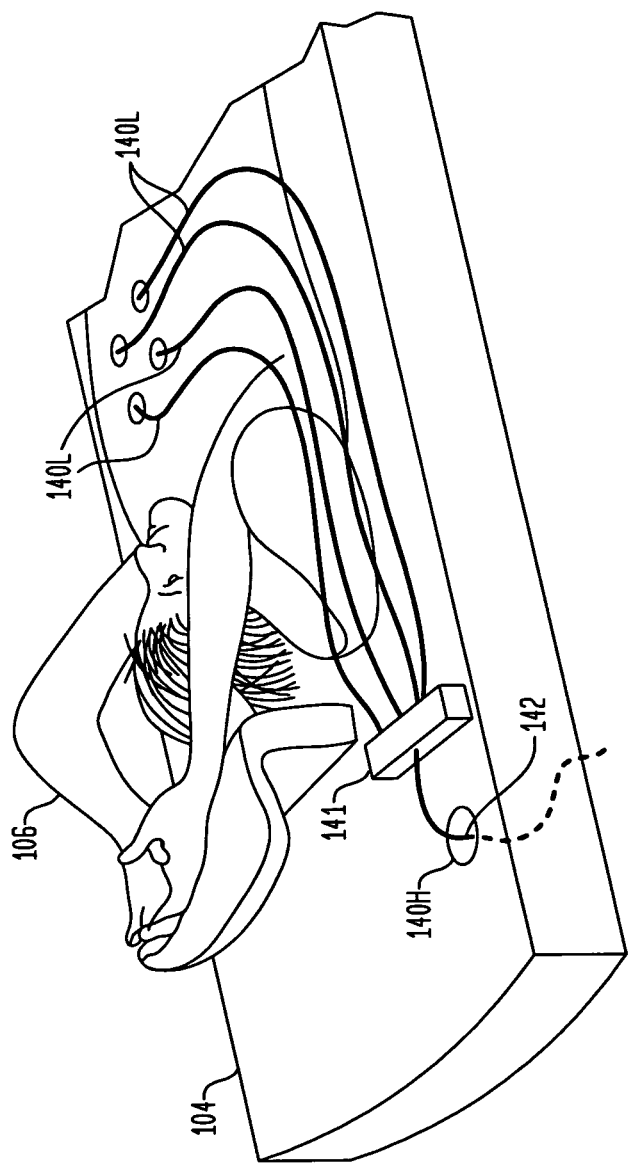

MEDICAL IMAGING SYSTEM WITH INTEGRATED BODY MONITORING DEVICE

RELATED APPLICATIONS

The present patent document claims the benefit of the filing date under 35 U.S.C. §119(e) of provisional U.S. patent application Ser. No. 60/583,441, filed Jun. 28, 2004, which is hereby incorporated by reference.

BACKGROUND

Field of the Invention

The present invention relates generally to medical imaging systems and, more particularly, to the use of medical imaging systems, such as, e.g., nuclear medical imaging systems along with body monitoring devices, such as, e.g., electrocardiogram devices.

The Background

A variety of medical imaging systems are known. Some illustrative imaging systems include nuclear medical imaging systems (e.g., gamma cameras), computed tomography (CT or CAT) systems, magnetic resonance imaging (MRI) systems, positron-emission tomography (PET) systems, ultrasound systems and/or the like.

With respect to nuclear medical imaging systems, nuclear medicine is a unique medical specialty wherein radiation (e.g., gamma radiation) is used to acquire images that show, e.g., the function and/or anatomy of organs, bones and/or tissues of the body. Typically, radioactive compounds, called radiopharmaceuticals or tracers, are introduced into the body, either by injection or ingestion, and are attracted to specific organs, bones or tissues of interest. These radiopharmaceuticals produce gamma photon emissions that emanate from the body and are captured by a scintillation crystal, with which the photons interact to produce flashes of light or "events." These events can be detected by, e.g., an array of photo-detectors, such as photomultiplier tubes, and their spatial locations or positions can be calculated and stored. In this manner, an image of an organ, tissue or the like under study can be created from detection of the distribution of the radioisotopes in the body.

Typically, this type of nuclear medical imaging equipment, called a gamma camera or a scintillation camera, includes one or more detectors that are enclosed within a metal housing. The positions of the detectors can typically be changed to a variety of orientations to obtain images of a patient's body from various directions. In many instances, a data acquisition console (e.g., with a user interface and/or display) is located proximate a patient during use for a technologist to manipulate during data acquisition. In addition to the data acquisition console, images are often developed via a processing computer system which is operated at another image processing computer console including, e.g., an operator interface and a display, which may often be located in another room, to develop images. By way of example, the image acquisition data may, in some instances, be transmitted to the processing computer system after acquisition using the acquisition console.

In some applications, nuclear medical imaging systems can be used in conjunction with an electrocardiogram (ECG) device in order to perform specific types of analyses. For example, in some instances, heart-wall motion and/or overall heart function can be analyzed using a technique known as cardiac gating. Cardiac gating typically involves the use of an electric signal from the pumping of the heart to control and/or obtain images of, e.g., heart contractions. In cardiac gating, images of the heart can be synchronized with different parts of the cardiac cycle. An ECG can record electrical currents that activate a patient's heart muscle in order to determine these parts of the cardiac cycle.

A typical electrocardiogram (ECG) includes electrode patches that are attached to a patient's skin (e.g., with adhesives) to measure electrical impulses of a patient's heart. The electrode patches are connected to the ECG device with long conductive wires (e.g., leads) that extend to the ECG device itself. Typically, the leads need to be rather long in order to enable doctors, radiologists, technologists and/or the like to move them to desired locations during use and/or to ensure that the leads are non-obstructive during a desired procedure. The electrical impulses received by the electrodes are transmitted via the conductive leads and processed by the ECG. Often, the impulses are recorded in wave forms which can be displayed, e.g., on a display, such as, e.g., a computer monitor or the like, such as, e.g., in alphanumeric representations and/or as a graphical representation of the wave forms (e.g., heart-pulse histograms). Waveforms may represent, e.g., currents in a different area of a patient's heart, such as, e.g., electrical current in the atria (i.e., the upper chambers of the heart) and/or the ventricles (i.e., the lower chambers of the heart). Among other things, an ECG can be used to measure heart rate, heart rhythm, heart wave patterns and/or the like.

While the importance of nuclear cardiology has grown steadily over the last few decades, relatively recently, gated single photon emission computed tomography (SPECT) has emerged as an important method for, inter alia, myocardial perfusion imaging through concurrent display and analysis of myocardial perfusion and contractile functions. Gated SPECT typically involves an image acquisition technique in which a patient's ECG data is used to control acquisition. In some examples, a data acquisition computer system (which may be the same as or different from the image processing computer system discussed above) can be used to define a number of frames in which an RR interval (e.g., the interval between two subsequent R-peaks) is to be divided (such as, e.g., 8 frames, 16 frames or another number of frames). The ECG can be connected to the computer system and the RR intervals (over a time period of about, e.g., a minute or less) can be obtained and, e.g., displayed graphically as a histogram. Typically, a window (such as, e.g., between about 10-20 percent) is selected around a mean RR interval, such that only data from cardiac cycles within that window are accepted. Then, during acquisition, the computer system can be used to analyze the R waves and check if the RR interval is within the established window limits. The data from the first frame of the cardiac cycle is stored in frame 1, the data from the second frame is stored in frame 2, and so on. Upon reaching a predefined acquisition time and angle, the camera can be controlled to move to a new position (such as, e.g., a few degrees to a subsequent angular position within an acquisition path). This procedure can be repeated over the acquisition path, such as, e.g., over about 180 degrees in some instances.

While gated SPECT procedures, employing both gamma cameras and ECG devices, have proven to be very valuable, the co-use of such systems has been problematic. Among other things, the above-described long conductive wires (e.g., leads) of the ECG device can be obstructive, distractive and/or be a nuisance during use. These problems are exacerbated by the fact that gamma cameras typically involve the use of movable platforms upon which a patient is supported during image acquisition. Movement of the platform while leads are physically attached to an individual can result in the risk that leads may become entangled in equipment, snag and/or tug on individuals and/or equipment, resulting in potential equipment problems and/or the like. Thus, while wires need to be long for freedom of movement, the increased length increases their intrusive nature and also increases the likelihood of becoming caught in equipment or the like.

In addition, the concurrent use of such gamma cameras and ECG equipment by physicians and the like can be somewhat cumbersome because the devices are separate. Often, the ECG's display and/or user interface will be displaced from the nuclear medical equipment's display and/or user interface. Accordingly, operation of the equipment together can be problematic. Moreover, because the ECG device is usually a separate unit that can be placed on the side of the imaging system during use, while the patient is positioned on an imaging platform (e.g., imaging table) that moves relative to the ECG during the patient set-up and, sometimes, even during acquisition, operating around and/or with the ECG equipment can be cumbersome and/or problematic. Because the ECG device is separate, it creates additional clutter that may be in the way of the patient or technologist, etc., during use. Moreover, because the ECG device is separate, it is often in a non-ideal location for the technologist to view and/or manipulate the ECG equipment.

Thus, while a variety of systems and methods are known, there remains a continued need for improved systems and methods overcoming the above and/or other problems with existing systems and methods.

BRIEF DESCRIPTION OF THE DRAWINGS

The preferred embodiments of the present invention are shown by a way of example, and not limitation, in the accompanying figures, in which:

FIG. 2(B) is a side view of a medical imagining system with an integrated body monitoring device according to some preferred embodiments of the invention in which the components of an ECG device are mounted so as to move along with movement of a patient support platform;

FIG. 3 is a perspective view demonstrating an illustrative example of a patient upon a movable platform according to some preferred embodiments of the invention;

FIGS. 4(A)-4(C) are partially broken away side views demonstrating some illustrative communication mechanisms for transmitting signals from a vicinity of a moving platform, wherein FIG. 4(A) illustrates the use of a pulley system for wiring or the like, FIG. 4(B) illustrates the use of a sliding contact, and FIG. 4(C) illustrates the use of a wireless communication mechanism.

SUMMARY OF THE PREFERRED EMBODIMENTS

Figure 1:
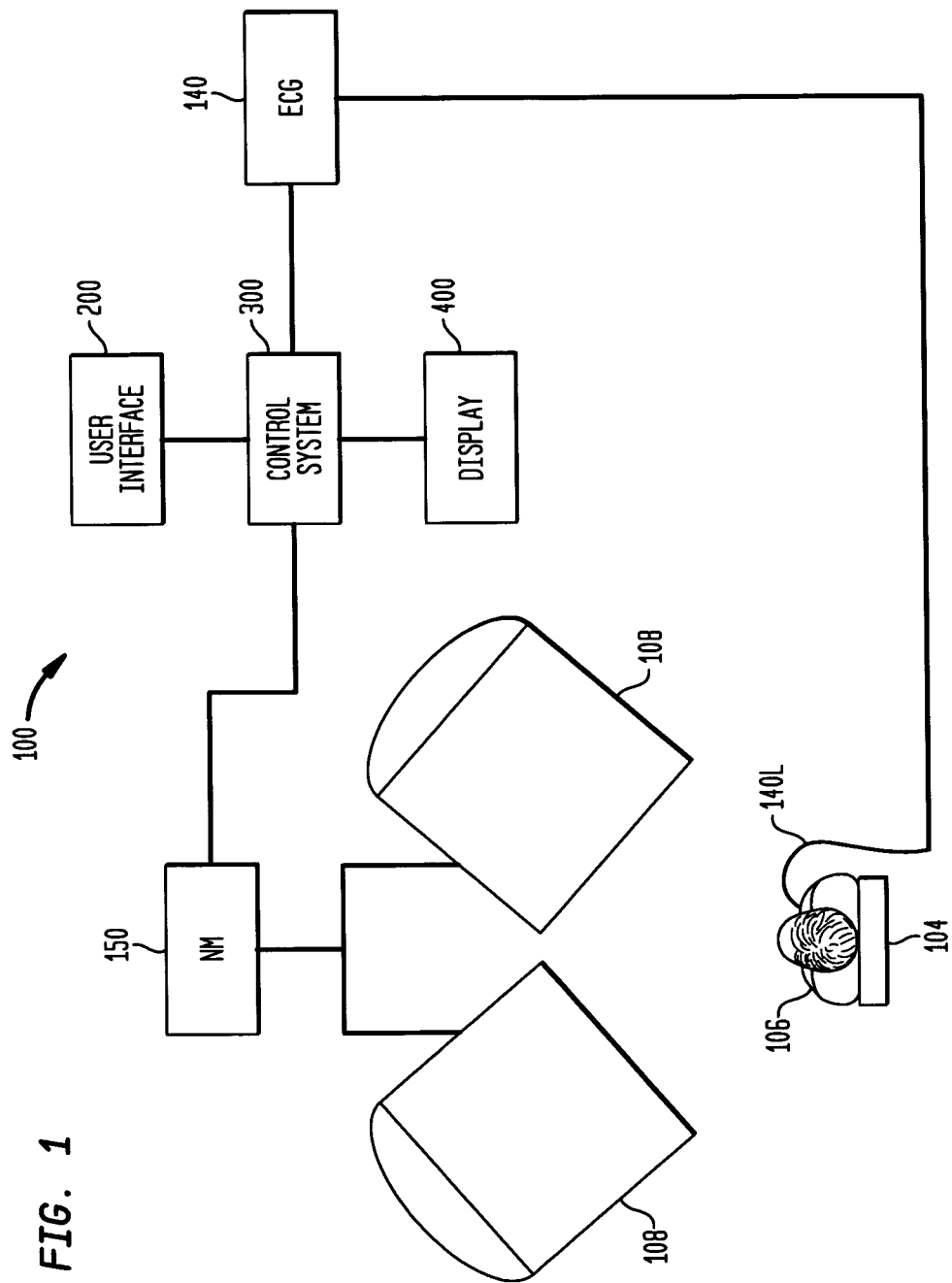
FIG. 1 is a schematic diagram of a medical imagining system with an integrated body monitoring device according to some preferred embodiments of the invention.

The preferred embodiments of the present invention can significantly improve upon existing methods and/or apparatuses.

According to some preferred embodiments of the invention, a medical imaging system with an integrated body monitoring device is provided that includes: a movable platform for supporting a patient during image acquisition; an image acquisition device for the acquisition of images of the patient upon the platform; a body monitoring device for the monitoring of a body function of the patient during image acquisition; the body monitoring device being adapted to transmit body function signals to the image acquisition device and the image acquisition device being adapted to effect image acquisition based on the signals received from the body monitoring device; wherein the body monitoring device is integrated with the image acquisition system.

In the preferred embodiments, the medical imaging system is a nuclear medical imaging system and the body monitoring device is an ECG device. In the preferred embodiments, the ECG device is mounted on or within a housing of the nuclear medical imaging system. Preferably, the medical imaging system includes at least one display adapted to display ECG data and nuclear medical imaging data substantially concurrently within an operating region for a technologist during data acquisition and, more preferably, the ECG data and the nuclear medical imaging data are concurrently displayed at the same time on the same monitor together. In the preferred embodiments, the ECG device includes at least one wire connected to at least one electrode, wherein the at least one wire is fixedly connected within or to the platform or a support of the platform so as not to extend significantly from a side of the platform during use such that risk of snagging on equipment is minimized. Preferably, means for reducing slack within the at least one wire during movement of the platform is provided.

According to other embodiments of the invention, a method of using a medical imaging system with an integrated body monitoring device is performed that includes: situating a patient upon a movable platform for image acquisition; initiating image acquisition with an image acquisition device to obtain images of the patient upon the platform; monitoring a body function of the patient with a body monitoring device during image acquisition; transmitting body function signals from the body monitoring device to the image acquisition device using a communication mechanism that is integrated with the medical imaging system and that avoids obstructing access around both sides of the movable platform; controlling image acquisition with the image acquisition device based on the signals received from the body monitoring device.

In some preferred embodiments, the transmitting using a communication mechanism that is integrated with the medical imaging system includes transmitting via at least one wire that does not extend significantly from a side of the platform during use such that risk of snagging on equipment is minimized. In some preferred embodiments, the transmitting using a communication mechanism that is integrated with the medical imaging system includes transmitting via a wireless transmitter supported to move along with the platform during use and a wireless receiver configured to receive communication signals from the wireless transmitter for communications to an ECG. In preferred embodiments, the method further includes displaying ECG data and nuclear medical imaging data substantially concurrently within an operating region for a technologist during data acquisition and, most preferably, displaying the ECG data and the nuclear medical imaging data concurrently on the same monitor.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

According to some preferred embodiments of the present invention, a medical imaging system (such as, e.g., a nuclear medical imaging system) is provided with an integrated body monitoring device (such as, e.g., an ECG device). While the most preferred embodiments involve the implementation of an ECG device in a nuclear medical imaging system, it should be understood based on this disclosure that the principles herein can be employed in relation to a variety of other imaging systems and/or body monitoring devices. As explained above, some illustrative imaging systems can include nuclear medical imaging systems, CT or CAT systems, MRI systems, PET systems, ultrasound systems and/or the like.

With respect to other body monitoring devices, any apparatus or system that provides an output representative of body functioning may be employed in some other embodiments of the invention. By way of example, body monitoring devices can include various devices that monitor breathing and/or assorted other bodily functions (by way of example, body monitoring devices can monitor, inter alia, acoustics or sound, air-flow [e.g., nasal or oral], body temperature, pulmonary activity and/or various other measurable qualities). In this disclosure, the terminology body function gated refers to the controlling of data acquisition based upon some form of body function, such as, e.g., cardiac gating described above.

According to some preferred embodiments, an ECG is integrated into a nuclear medical imaging system in such a manner that the patient data can be displayed proximate to the other patient data of the imaging system. In addition, the ECG device can also preferably be readily manipulated from the same user location or operating region as the imaging system. Preferably, the ECG data and the imaging system data are displayed using side-by-side displays or, more preferably, the same display, such as, e.g., the same monitor and the ECG device and the imaging system are manipulated using the same user interface.

According to some preferred embodiments, the ECG device is integrated with the imaging system in such a manner that its wires (e.g. leads) are inhibited from becoming entangled in equipment, detaching from a patient and/or the like, such as, e.g., by integrating its wiring or the like into the imaging system's structure. In some embodiments, the ECG wires (e.g. leads) that connect to the patient are plugged into an electrical connector or outlet mounted on a movable platform upon which the user is movably supported. In some embodiments, the platform can be mounted for a) fore-and-aft movement in a generally horizontal direction, b) up-and-down movement in a generally vertical direction, c) combinations thereof and/or d) the like. The platform can include, e.g., a bed upon which a user rests, a chair upon which a user sits, and/or any other type of support. The platform can include any appropriate structure known in the art and can be moved via any known platform moving mechanism(s) known in the art.

In some embodiments, with the ECG's electrode wires (e.g., leads) plugged into an electrical connector mounted on the movable platform, the electrical connections can be readily routed to the ECG device in a non-intrusive manner. As described below, a variety of communication mechanisms (e.g., both wired and wireless mechanisms) for routing the electrical connections to the ECG device can be employed. In this manner, the ECG wires (e.g., leads) can have a minimal length so as to avoid excess slack and to minimize risks that such leads may become entangled in the equipment or the like. By way of example, in some embodiments, the leads can have a length of about 4 feet or less, or even about 3 feet or less, or even about 2½ feet or less from the electrode pads to the electrical connector.

Illustrative embodiments depicting an ECG device integrated within a nuclear medical imaging system will now be described with reference to FIGS. 1-5. Reference is first made to FIG. 2 which shows, inter alia, illustrative components of a nuclear medical imaging device, such as, e.g., a gantry 102 disposed above a movable platform or table 104 upon which a patient 106 may be placed while undergoing imaging. The patient 106 may be placed in a variety of positions or orientations during imaging, depending on the particular needs of the imaging process. The patient 106 may be placed, e.g., on his or her back, stomach, left or right side, in a position intermediate these positions, and/or in a variety of other positions by, e.g., altering the structure of the platform and/or providing appropriate supports. As shown, at least one photo-detector 108 is mounted on the gantry 102 for performing imaging.

In the preferred embodiments, the photo-detector(s) can detect electromagnetic radiation emitted from, e.g., radio-active isotopes or the like within a patient 106 or the like. The photo-detector(s) 108 can include, e.g., gamma scintillation cameras or the like that pick up, e.g., gamma rays emitted by the isotopes. By way of example, while the patient 106 lies motionless on the platform 104, gamma scintillation cameras can be used to acquire images and record them on a computer for analysis.

FIG. 1 is a schematic representation of an illustrative system in accordance with some preferred embodiments in which a system includes; a nuclear medical imaging device including NM processing components 150, detectors 108 and a movable platform 104 for supporting a patient 106; a control system 300 (such as, e.g., one or more computer, including, e.g., processor(s), memory, data storage, I/O ports, etc., which may be programmed so as to carry out desired functionality of some of the embodiments described herein); a user interface 200; a display 400; and an integrated ECG device 140. As demonstrated in this schematic diagram, in this preferred construction, a control system is used for processing related to both the nuclear medial imaging device data, etc., and the ECG data, etc. In this embodiment, a technologist 107 or the like (shown in FIGS. 2(A), 2(B) and 5) can operate both the ECG and the nuclear medical device from the same user interface 200 (which can include, e.g., keys, buttons, control elements, a graphical user interface (GUI) and/or any other appropriate means for user interfacing). In preferred embodiments, at least one, preferably a plurality, and in some embodiments all of the same keys, buttons, control elements and/or the like of the user interface that are used for operating the nuclear medical device can also be used for operating the ECG. In some illustrative examples, the user interface can include a standard computer keyboard and/or mouse (i.e., or other GUI pointer manipulating mechanism).

As also depicted in FIG. 1, in these embodiments, the technologist can also control and/or view outputs displayed substantially concurrently using the user interface 200 and the display 400. As shown, the control system 300 can be used to display, e.g., data and information related to both the NM device 150 and the ECG device 140 using the same display 400. In some embodiments, the display can be used to alternatively display content from the respective devices in a substantially concurrent, but alternating manner. However, in more preferred embodiments, data from both devices can be displayed concurrently at the same time (see discussion below with respect to FIG. 5).

Figure 2A:
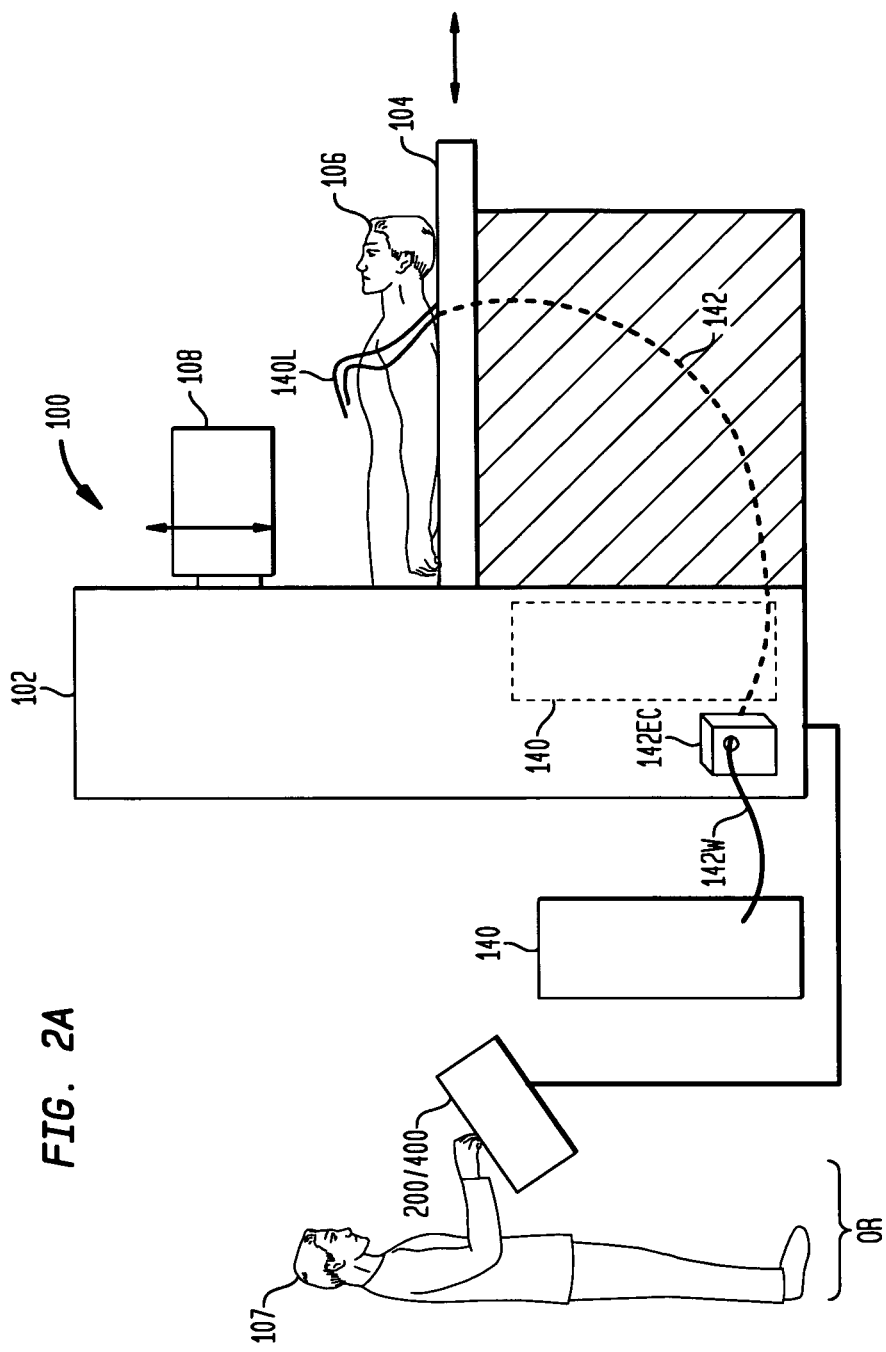
FIG. 2(A) is a side view of a medical imagining system with an integrated body monitoring device according to some preferred embodiments of the invention.

The embodiment depicted in FIG. 2(A) is similar to that shown in FIG. 1. Although not shown in FIG. 2(A), the nuclear medical imaging apparatus can include a separate computer system (not shown) to carryout processing of data. In some embodiments that nuclear medical imaging apparatus can include computing capabilities integrated in the device, such as, e.g., mounted on the gantry 102 and/or another component of the system. In addition to the nuclear medical imaging components shown in FIG. 2(A), which were already described above, FIG. 2(A) illustrates components related to the integration of an ECG device according to some embodiments. In that regard, as shown, an ECG device 140, which may include some or all of the components of a standard ECG device (such as, e.g., a processor, ECG hardware, ECG software, etc.), is located either adjacent or proximate the nuclear medical device (e.g., adjacent or proximate the gantry and/or another component) or is located within or is physically attached to the nuclear medical device (e.g., within or attached to the gantry and/or another component thereof).

As shown in FIG. 2(A), wires (e.g., leads) 140L which are attached to a patient 106 communicate with the ECG device 140 via communication medium 142, which can include, e.g., a radio frequency (RF) signal, an insulated metal wire, a coaxial cable, a twisted pair, an optical fiber and/or another appropriate medium. In this disclosure, the terminology "wire" is defined to broadly encompass any form of transmission over an medium other than air alone, such as, e.g., via a coaxial cable, a twisted pair, a fiber, a lead and/or the like. On the other hand, in this disclosure, the terminology "wireless" is defined to broadly encompass any form of transmission over air alone. FIG. 2(A) illustrates that the ECG device can be separate from the nuclear medical imaging system (e.g., having its own housing or enclosure containing ECG hardware, etc.), as shown in solid lines, or can be mounted to or contained within the nuclear medical imaging system (e.g., contained within a housing of the nuclear medical imaging system and/or attached thereto), such as, e.g., mounted to or contained within the gantry housing, or mounted to or contained within a control unit or console operatively connected to the gantry, etc., such as shown in dashed lines.

In embodiments wherein the ECG device is separate from the nuclear imaging medical system structure, the nuclear imaging medical system structure may include an electrical connector 142EC, as shown in FIG. 2(A). The electrical connector preferably is configured to enable the ECG to readily plug into or connect to the electrical connector, such as, e.g., using electrical wiring 142W, as shown in FIG. 2(A). In some embodiments, however, the electrical wiring can be replaced with any other known wireless method of sending digital signals, such as, e.g., RF transmissions and the like. In some preferred embodiments, the ECG can receive electrical power for its operation via its connection to the nuclear medical imaging device, such as, e.g., using electrical wiring 142W and/or the ECG can be otherwise commonly powered with the nuclear medical imaging device. It should be understood that the wiring 142W can include a plurality of separate lines (e.g., one or more signal lines, one or more power lines, etc.) as may be needed depending on circumstances.

In operation, a technologist or the like can preferably operate the ECG and/or the nuclear medical imaging device from within a common operator region OR as shown in FIG. 2(A). From this operating region, the technologist or the like can preferably perform, among other operations, gated SPECT procedures and/or the like. Preferably, the technologist 107 or the like can access the user interface 200 and/or the display 400 from within this operating region OR. Preferably, the operating region is sized such that the respective displays of the ECG information and the nuclear medical imaging device information are each within about an arm's length of the technologist, and, are each preferably less than about 3 feet apart from one another, or, more preferably, less than about 2 feet apart, or, more preferably, less than about 1 foot apart, in some illustrative embodiments. While, in some embodiments, the display of the ECG information and the nuclear medical imaging device information can be on separate displays that are proximate one another, in the most preferred embodiments, the information can be displayed on the same display or monitor, such as, e.g., a CRT display, a liquid crystal display and/or any other form of display.

In the embodiments shown in FIG. 2(A), as represented by the arrows A, the platform can be moved at least horizontally fore-and-aft. In these embodiments, the detectors 108 are also movable as represented by the arrows B (such as, e.g., in a generally rotational path around an axis that is parallel to the direction of the arrows A). Nevertheless, despite these movements of the equipment, there is essentially no concern that ECG wires (e.g., leads) or the like may become entangled in the system.

FIG. 2(B) shows an alternate embodiment that is generally similar to the embodiment shown in FIG. 2(A), with the exception that the ECG device is mounted so as to move along with (e.g., in unison with) the platform 104. Among other things, this may enable the ECG device to be conveniently located for the technologist or the like during use. At the same time, this may also facilitate communication from the wires (e.g., leads) 140L to the ECG device since the wires (e.g., leads) 140L will not have to move relatively to the ECG device. While FIG. 2(B) shows the ECG device mounted to an underside of the platform 104, it is contemplated that in other embodiments the ECG device can be mounted in a different manner so as to move along with the platform (such as, e.g., being attached to an end of the platform, above the platform and/or the like).

FIG. 3 shows one illustrative method of mounting the wires (e.g., leads) 140L to the system in some illustrative embodiments. As demonstrated, the wires or leads do not have to be long, but can be only a few feet long. In addition, as demonstrated, the wires or leads do not have to extend over or substantially over a side of the platform 104, such that physicians, technologists, etc., can freely pass there-around without difficulty or increased risk of snagging the wires or leads. As shown in FIG. 104, the wires or leads 140L can, if desired, be connected to an electrical connector 141, which in turn connects to the communication medium 142. Once again, the communication medium can include a plurality of independent lines, such that the various signals from the wires or leads 140L can be carried individually in preferred embodiments. Although FIG. 3 illustrates the use of a hole 140H extending through the platform 140L, in some other embodiments, the wires or leads 140L can pass around a side or end of the platform. Additionally, although FIG. 3 shows one illustrated linear path 142, it should be understood that this path may include a plurality of lines and/or may even include each of the wires or leads 140L (e.g., the four lead lines shown in the example of FIG. 3) continuing onward together (e.g., whether through the hole 140H, around the side of the platform 104 or the like) toward or even all of the way to ECG device.

Figure 4A:
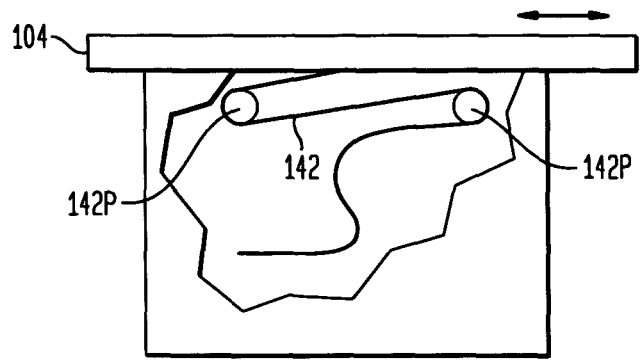
Figure 4B:
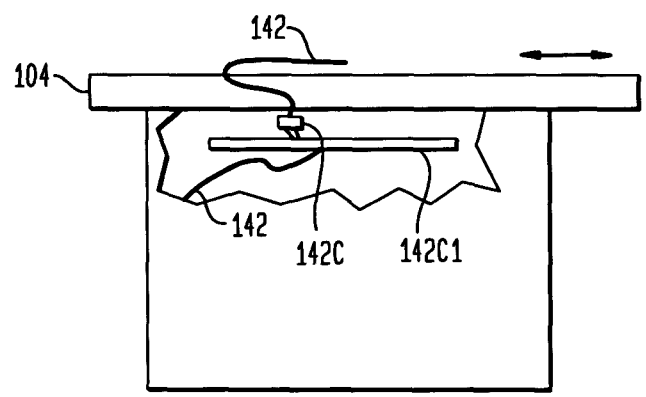
Figure 4C:
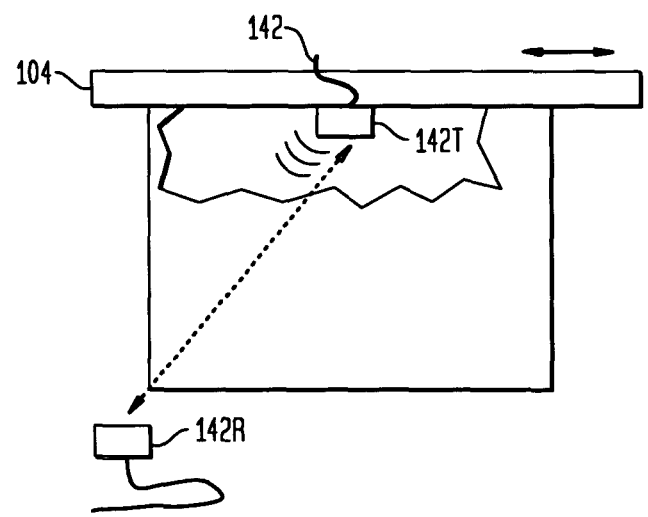

FIGS. 4(A)-4(C) show some illustrative methods for providing the communication medium or mechanism 142 between the wires or leads 140L and the ECG device 140. In this regard, FIGS. 4(A)-4(C) are partially broken away side views demonstrating some illustrative methods for transmitting signals from a vicinity of a moving platform to the ECG device. FIG. 4(A) illustrates the use of a pulley system for wiring or the like. FIG. 4(B) illustrates the use of a sliding contact. And, FIG. 4(C) illustrates the use of a wireless transmission. The embodiments shown in FIGS. 4(A) and 4(B) have some benefits in that the solid, physical connection can provide a more secure and reliable transmission. Such security and reliability may be advantageous in medical technologies demanding a high level of security and reliability. Furthermore, the embodiment shown in FIG. 4(A) may have a highest level of security and reliability since the communication medium or mechanism may essentially be un-separated, while the sliding contact FIG. 4(B) requires maintained pressure to ensure that the separated elements remain in contact. Additionally, the embodiment shown in FIG. 4(A) can be less subject to wear potential.

More specifically, FIG. 4(A) shows an embodiment in which the medium or mechanism (which may, e.g., include one or more lines) extends beneath the platform (e.g., possibly within an enclosure directly beneath the platform), such as, e.g., through a hole 140H in some examples. At this position under the platform, the medium 142 may extend around one or more pulleys 142P that operate as a means for reducing slack. The pulleys 142P can include one or more pulley that is biased in one or more directions (such as, e.g., using one or more springs) so as to remove slack within the medium 142, such as, e.g., when the medium 142 involves wires of some sort. Although not shown, a variety of other means for reducing slack can be used, including, e.g., a spool upon which excess wire or the like can be wound and/or unwound in accordance with the motion of the platform 104.

On the other hand, FIG. 4(B) shows an embodiment in which the medium 142 (or the wires or leads 140L themselves) connect(s) to a sliding contact element 142C (such as, e.g., a metal spring, plate, brush or the like) which rests upon an electrical contact plate 142C1 in such a manner as to slide along the plate 142C1 with movement of the platform while maintaining electrical communication via this sliding contact.

On yet another hand, FIG. 4(C) shows another embodiment in which the medium (or the wires or leads 140L themselves) connect(s) to a transmitter unit 142T and sends a wireless transmission to a receiving unit 142R (which receiving unit can be located at any appropriate location, such as, e.g., proximate the ECG device). This embodiment has some advantages in avoiding snagging problems, but can also have attendant security and reliability limitations as compared to wired communications. Although FIG. 4(C) shows the transmitter unit 142T fixedly connected to the platform 104, a transmitter unit can be located in any other location that moves with the platform 104 and/or patient 106, including even, e.g., upon the patient himself or herself. By way of example, the system may employ BLUETOOTH technology so as to transmit signals to ECG devices. By way of example, technology similar to the LIFESYNC wireless ECG system released by GMP WIRELESS MEDICINE, INC. on Mar. 30, 2004 can be employed in some embodiments. The "LifeSync® System eliminates lead wires and trunk cables between patients and bedside, 12-lead or transport ECG monitors, allowing freedom of movement throughout the hospital. Using highly-sophisticated Bluetooth® wireless technology*, the LifeSync® System employs two-way radios to collect and transmit patient ECG and respiration data to the hospitals existing ECG monitors." See: [http://www.wirelessecg.com/about_lifesync/index.html].

Figure 5:
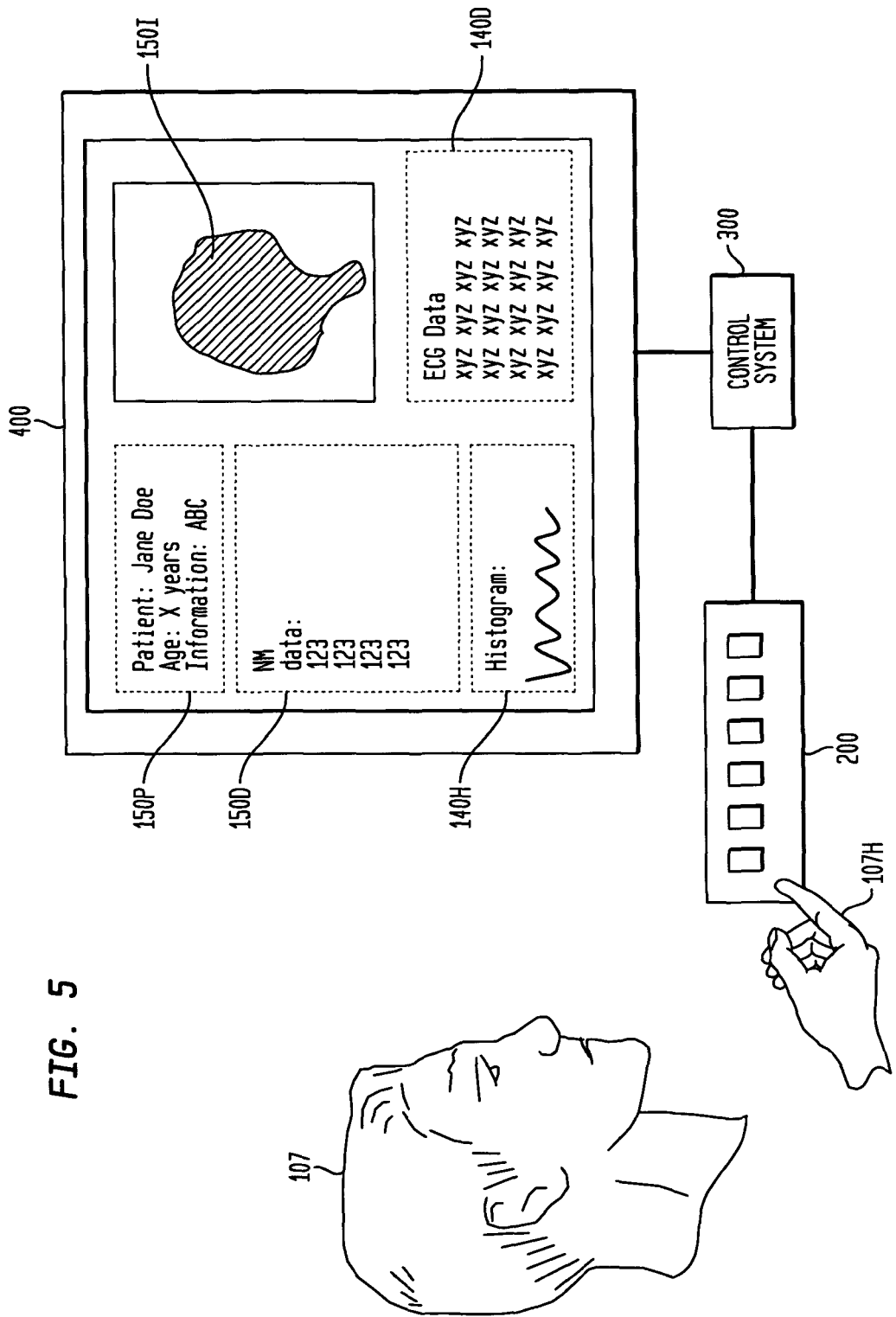
FIG. 5 is a schematic diagram demonstrating a user proximate a display and a user interface according to some embodiments of the invention.

FIG. 5 demonstrates other notable features of some embodiments of the present invention which incorporate nuclear medical imaging functionality together with ECG functionality as an integrated system. Among other things, the system shown in FIG. 5 can greatly facilitate a technologists operation of the nuclear medical system and the ECG system concurrently during a data acquisition phase of operation. In this regard, FIG. 5 shows how, in some preferred embodiments, a technologist or the like 107 can readily access both the user interface 200, which is, as described above, preferably used to control both the ECG and nuclear medical imaging system functionality and/or display of output results related to the ECG and nuclear medical imaging system. For example, a technologist or physician 107 can preferably manipulate the interface 200 by his or her hand 107H while located in a limited operating region (such as, e.g., without requiring the individual to walk or even to step over to a new position).

In addition, FIG. 5 also shows how, in some preferred embodiments, a technologist or the like 107 can easily view both ECG data and nuclear medical imaging date concurrently at the same time on the same display or monitor 400. In this regard, the ECG data 140D displayed may include, by way of example, pulse data, respiration data, other body function data, a graphical representation of the acquisition data (such as, e.g., a histogram 140H as shown) and/or the like. In addition, the nuclear medical imaging data 150D may include, e.g., image data, image acquisition data, detector position data, etc., as well as patient information data 150P and detector images, such as, e.g., 150I (showing, e.g., a pictorial image display of an image acquired). The dot-and-dash lines shown on the display or monitor 400 illustrate that, in some embodiments, the displayed information can be compartmentalized into sub-regions of the display or monitor if desired.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure and during the prosecution of this case, the following abbreviated terminology may be employed: "e.g." which means "for example."

What is claimed is:

1. A medical imaging system with an integrated body monitoring device, comprising:
   a movable platform for supporting a patient during image acquisition;
   a connector mounted to the movable platform and configured to connect to electrodes attached to the patient via leads, the connector being mounted such that it moves together with the movable platform, and wherein the platform together with the connector are movable in at least a generally horizontal direction;
   an image acquisition device for the acquisition of images of the patient upon the platform;
   a body monitoring device for the monitoring of a body function of the patient during image acquisition via signals from said electrodes, said body monitoring device being configured to receive said signals through a communication medium coupled to said connector;
   a control system for controlling operation of both said image acquisition device and said body monitoring device; and
   a user interface, coupled to said control system, from which a user is able to operate both said image acquisition device and said body monitoring device.

2. The medical imaging system with an integrated body monitoring device of claim 1, wherein said body monitoring device is an ECG device.

3. The medical imaging system with an integrated body monitoring device of claim 1, wherein said communication medium comprises a wire having a sliding contact engagement.

4. The medical imaging system with an integrated body monitoring device of claim 1, wherein said image acquisition device comprises a gamma camera.

5. The medical imaging system with an integrated body monitoring device of claim 4, wherein said body monitoring device is an ECG device, and said ECG device is mounted on or within a support for said gamma camera.

6. The medical imaging system with an integrated body monitoring device of claim 1, wherein said communication medium comprises a wire and includes a mechanism configured to reduce slack within said wire during movement of said platform.

7. The medical imaging system with an integrated body monitoring device of claim 6, wherein said mechanism configured to reduce slack includes a pulley system beneath said platform for reducing slack within said wire.

8. The medical imaging system with an integrated body monitoring device of claim 1, wherein said communication medium comprises a wireless transmitter connected to said connector, and a wireless receiver configured to receive communication signals from said wireless transmitter for communication to said body monitoring device.

9. The medical imaging system of claim 8, wherein said transmitter is part of a first transceiver and said receiver is part of a second transceiver.

10. The medical imaging system with an integrated body monitoring device of claim 1, wherein said medical imaging system is a nuclear medical imaging system.

11. The medical imaging system with an integrated body monitoring device of claim 10, wherein said body monitoring device is an ECG device and said signals are cardiac signals.

12. The medical imaging system with an integrated body monitoring device of claim 11, wherein said medical imaging system includes at least one display adapted to display ECG data and nuclear medical imaging data substantially concurrently within an operating region for a technologist during data acquisition.

13. The medical imaging system with an integrated body monitoring device of claim 12, wherein said ECG data and said nuclear medical imaging data are concurrently displayed at the same time on the same monitor together.

14. The medical imaging system with an integrated body monitoring device of claim 11, wherein said ECG device is mounted to said movable platform.

15. The medical imaging system with an integrated body monitoring device of claim 13, wherein said ECG data includes bodily function acquisition data.

16. The medical imaging system with an integrated body monitoring device of claim 13, wherein said ECG data includes pulse data.

17. A medical imaging system with an integrated body monitoring device, comprising:
   a movable platform for supporting a patient during image acquisition;
   a connector mounted to the moveable platform and configured to connect to a body monitoring device and mounted such that it moves together with the moveable platform;
   an image acquisition device for the acquisition of images of the patient upon the platform;
   a support mechanism for said image acquisition device; and
   a body monitoring device mounted to the movable platform and configured to receive monitoring signals from a wire coupled to the patient and to process said signals for monitoring of a body function of the patient during image acquisition, wherein the platform together with the body monitoring device and the connector are movable in at least a horizontal direction.

18. The medical imaging system of claim 17, further comprising:

a control system for controlling operation of both said image acquisition device and said body monitoring device; and a user interface, coupled to said control system, from which a user is able to operate both said image acquisition device and said body monitoring device.

19. The medical imaging system of claim 17, further comprising a display device for displaying monitored body function data and medical image data.

20. A medical imaging system with an integrated body monitoring device, comprising:

a movable platform for supporting a patient during image acquisition;

a connector mounted to the moveable platform and configured to connect to a body monitoring device and mounted such that it moves together with the moveable platform;

an image acquisition device for the acquisition of images of the patient upon the platform;

a support mechanism for said image acquisition device; and a body monitoring device mounted in or on the support mechanism and configured to receive monitoring signals from a wire coupled to the patient and to process said signals for monitoring of a body function of the patient during image acquisition, wherein the platform together with the body monitoring device and the connector are movable in at least a horizontal direction.

21. The medical imaging system as set forth in claim 20, wherein said body monitoring device comprises an ECG device.

22. The medical imaging system as set forth in claim 21, wherein the wire is coupled to the patient via at least one electrode attached to the patient, the system further comprising a communication medium coupling said wire to said ECG device.

23. The medical imaging system as set forth in claim 22, wherein said communication medium comprises a communication medium wire and includes a mechanism configured to reduce slack within the communication medium wire during movement of said platform.

24. The medical imaging system as set forth in claim 23, wherein said mechanism configured to reduce slack includes a pulley system beneath said platform.

25. The medical imaging system as set forth in claim 22, wherein said communication medium comprises a wire having a sliding contact engagement.

26. The medical imaging system as set forth in claim 22, wherein said communication medium comprises a wireless transmitter connected to said wire, and a wireless receiver configured to receive communication signals from said wireless transmitter for communication to said ECG device.

* * * * *